(12) United States Patent
Mitra et al.

(10) Patent No.: US 8,142,818 B2
(45) Date of Patent: Mar. 27, 2012

(54) HERBAL COMPOSITION FOR THE PREVENTION OF WRINKLES AND SKIN DISORDERS, METHODS OF PREPARING THE SAME AND USES THEREOF

(75) Inventors: Shankar Kumar Mitra, Bangalore (IN); Ekta Saxena, Bangalore (IN)

(73) Assignee: Himalaya Global Holdings Limited, Dubai (AE)

( * ) Notice: Subject to any disclaimer, the term of this patent is extended or adjusted under 35 U.S.C. 154(b) by 81 days.

(21) Appl. No.: 12/440,917

(22) PCT Filed: Sep. 12, 2006

(86) PCT No.: PCT/IN2006/000347
§ 371 (c)(1),
(2), (4) Date: Mar. 11, 2009

(87) PCT Pub. No.: WO2008/032331
PCT Pub. Date: Mar. 20, 2008

(65) Prior Publication Data
US 2010/0040709 A1   Feb. 18, 2010

(51) Int. Cl.
*A61K 36/00* (2006.01)
(52) U.S. Cl. .................................................. 424/724
(58) Field of Classification Search .................... None
See application file for complete search history.

(56) References Cited

U.S. PATENT DOCUMENTS

| | | | |
|---|---|---|---|
| 5,236,679 A | 8/1993 | Wen et al. | |
| 5,595,756 A * | 1/1997 | Bally et al. | 424/450 |
| 6,224,850 B1 | 5/2001 | Breton et al. | |
| 6,455,077 B2 | 9/2002 | Katiyar et al. | |
| 6,815,553 B2 * | 11/2004 | Krasutsky et al. | 554/11 |
| 6,835,714 B1 | 12/2004 | Sato et al. | |
| 6,866,856 B2 | 3/2005 | Lu et al. | |
| 7,138,428 B2 * | 11/2006 | Lee et al. | 514/453 |
| 2002/0025349 A1 * | 2/2002 | Brindavanam et al. | 424/757 |
| 2003/0180395 A1 * | 9/2003 | Bueter | 424/725 |
| 2004/0028643 A1 | 2/2004 | Chiba et al. | |
| 2006/0177472 A1 | 8/2006 | Tomioka | |

FOREIGN PATENT DOCUMENTS

| EP | 0321180 | 12/1988 |
|---|---|---|
| JP | 4178324 | 6/1992 |

OTHER PUBLICATIONS

Manandhar et al. Plants and People of Napal; Timber Press, Inc. Portland, OR; p. 470.*
Phillipson, D. New Drugs From Nature—It Culd Be Yew; Phytotherapy Research; 13, 2-8 (1999).*
Raskin et al. Can an Apple a Day Keep the Doctor Away?; Current Pharmaceutical Design (10) 2004, pp. 3419-3429.*

(Continued)

*Primary Examiner* — Patricia Leith
(74) *Attorney, Agent, or Firm* — Knobbe, Martens, Olson & Bear, LLP

(57) ABSTRACT

Disclosed is a natural herbal composition for preventing wrinkles, skin roughness, dryness of skin, irregular pigmentation and brown spots due to aging, stress and environmental factors without any side effect. The composition comprises extracts of *Rhodomyrtus tomentosa*, *Cipadessa baccifera*, *Woodfordia fruticosa* and *Camellia sinensis*.

11 Claims, 15 Drawing Sheets

OTHER PUBLICATIONS

Revilla, E. Comparison of Several Procedures Used for the Extraction of Anthocyanins From Red Grapes; J. Agric. Food Chem (1999) (46) pp. 4592-4597.*

MacPhillamy, H.B. Plant Science Bulletin; Botanical Society of America, Inc, Apr. 1963, vol. 9, Issue 2, pp. 1-15.*

Blake, J. Tea's Potential Health Benefits Have Made It the New Hot Drink of Choice; Knight Ridder Tribune News Service; Washington: Feb. 16, 2004, p. 1 (pp. 1-6 of ProQuest Internet Database).*

Hiu et al. Two New Triterpenoids From Rhodomyrtus Tomentosa; Phytochemistry, 1976, vol. 15, pp. 1741-1743.*

King, J. and List, G. Ed. Supercritical Fluid Technology in Oil and Lipid Chemistry; AOCS Press, 1996, p. 216.*

Lust, J. The Herb Book; Bantam Books; New York, New York, 1974, pp. 38-39.*

Manandhar et al. Plants and People of Napal; Timber Press, Inc. Portland, OR; 2002, p. 470.*

International Search Report for PCT/IN2006/000347, mailed on Sep. 24, 2007, in 2 pages.

Mohiddin et al., "Traditional Medicinal Plants of Brunei Darussalam Part III. Sengkurong", *Int. J. Pharmacognosy*, vol. 30, 1992, No. 2, pp. 105-108.

Manandhar, N. 2002, in *Plants and People of Nepal*, pp. 153-154.

* cited by examiner

HERBAL COMPOSITION FOR THE PREVENTION OF WRINKLES AND SKIN DISORDERS, METHODS OF PREPARING THE SAME AND USES THEREOF

FIELD OF THE INVENTION

This invention, in general, relates to the field of cosmetology and in particular to a herbal cosmeceutical composition comprising novel plant extracts to protect the skin related disorders. More specifically, hut without restriction to the particular embodiments hereinafter described in accordance with the best mode of practice, this invention describes a novel skin care cosmeceutical composition comprising the extracts of *Rhodomyrtus tomentosa, Cipadessa baccifera, Woodfordia fruticosa*, alone or in combination with *Camellia sinensis*, and acceptable cosmeceutical formulation carriers, and methods of obtaining the same.

BACKGROUND OF THE INVENTION

Aging is a natural phenomenon of living organisms and the skin is the most affected organ during aging process in human beings. Wrinkling of the skin is usually the result of degeneration of the tissue fibers, loss of subcutaneous fat and loss of normal fluid content. Skin wrinkles are grooves in the skin and it can be on the surface of the skin or quite in deep.

Facial wrinkles of the upper one third of the face are common cosmetic concern and are caused by over activity of the underlying facial musculature in principle. Exposure to the sun induces clinical and histological changes to the skin, commonly called photo aging. Aging and photo aging may be manifested as wrinkles, skin roughness and dryness, irregular pigmentation and brown spots.

Wrinkle formation in the skin following long-term exposure of ultraviolet B irradiation is accompanied by decrease in skin elasticity and the curling of elastic fibers in the dermis. Quantitative and qualitative changes in dermal collagen and elastin occur in response to chronic ultraviolet (UV) irradiation.

One of the approaches to protect the human skin from the harmful effects of ultra violet radiation is to use antioxidants as photoprotectives. In recent years naturally occurring herbal compounds such as phenolic acids, flavonoids, and high molecular weight polyphenols have gained considerable attention as beneficial protective agents.

Wrinkle formation in the skin is accompanied by decrease in skin elasticity and the curling of elastic fibers in the dermis. Elastase inhibitors suppress the elastase activity and prevent the damage of dermal elastic fibers and might abolish wrinkle formation associated with the loss of skin elasticity. Also, in aging the balance between collagen synthesis and collagen fragmentation is altered. Collagenase enzyme inhibitors are also known to have potential role in preventing wrinkle formation.

Hyaluronic Acid (HA), a natural glycosaminoglycan biopolymer, is found in every tissue of the human body. It has an enormous water binding capacity (up to 1,000 times its weight) and it forms high viscosity hydrated polymers. More than 50% of the total amount of body HA is present in skin (in dermis and epidermis). Hyaluronic acid is a basic building block of the dermis. It stabilizes the intercellular structures of connective tissues and forms the elastoviscous fluid matrix in which collagen and elastin fibers are embedded. It also promotes the renewal of keratinocytes and its ability to retain water helps in proper hydration of the skin. The amount of HA in the skin decreases with aging and photo aging process.

Hyaluronidase is an enzyme that degrades HA resulting in reduced dermal hydration, disorganization of collagen and elastin fibers and increased skin wrinkling and folding. Hyaluronidase Inhibitors are known to have potential benefits in preventing and treating facial wrinkles.

RELATED ART

United States Patent Application No. 200400028643 to Chiba, Katsuyoshi et al. reveals a cosmetic composition for retarding skin aging comprising certain plant extracts for inhibition of melanin formation, elastase inhibition, hyaluronidase inhibition and antioxidants.

U.S. Pat. No. 6,224,850 to Breton et al. teaches the preparation of cosmetic compositions comprising plant extracts from the Iridaceae family.

U.S. Pat. No. 6,835,714 to Sato et al. demonstrates the use of heterocyclic compounds and their derivatives as elastase inhibitors.

U.S. Pat. No. 6,866,856 to Lu et al. reveals composition and delivery system for the treatment of wrinkles, fine lines and hyperhidrosis using plant extracts of the family Meliaceae.

SUMMARY OF THE INVENTION

It is a principal object of the present invention to provide a herbal cosmeceutical composition comprising novel skin protecting herbs in an effective concentration along with natural antioxidants. These and other objects are attained in accordance with the present invention wherein there is provided several embodiments for preparing a herbal cosmeceutical composition comprising the plant extracts of *Rhodomyrtus tomentosa, Cipadessa baccifera*, and *Woodfordia fruticosa*, alone or in combination thereof along with *Camellia sinensis* extract as an antioxidant and cosmeceutically acceptable carriers.

In accordance with one embodiment of the present invention, there is provided a herbal cosmeceutical composition, wherein said composition is effectively used for prevention and treatment of various skin disorders, viz. wrinkles, skin roughness, dryness of skin, irregular pigmentation and brown spots or other related disorders.

In accordance with another embodiment, there is provided a herbal cosmeceutical composition comprising extract of *Rhodomyrtus tomentosa, Cipadessa baccifera*, and *Woodfordia fruticosa*, alone or in combination thereof, wherein said composition is capable of inhibiting enzyme elastase, enzyme hyaluronidase, enzyme collagenase or other factors responsible for skin disorder.

In accordance with further embodiment of the present invention, there is provided a herbal cosmeceutical composition, wherein said composition additionally comprises a natural antioxidant *Camellia sinensis* to prevent the formation of ROS (Reactive Oxygen Species).

In yet another embodiment, the present invention provides a cosmetic preparation containing an effective concentration of extracts of plants *Rhodomyrtus tomentosa* and/or *Cipadessa baccifera* and/or *Woodfordia fruticosa* and *Camellia sinensis*. Said composition comprises said extracts of said plants in a cosmeceutically acceptable carrier or otherwise.

In one another embodiment, the present invention discloses methods of preparation of extracts from the plants *Rhodomyrtus tomentosa, Cipadessa baccifera, Woodfordia fruticosa* and *Camellia sinensis*.

In another embodiment, there is provided a method of preparation of extract from all parts of said plants, preferably aerial parts of *Rhodomyrtus tomentosa*, aerial parts of *Cipadessa baccifera*, fruits of *Woodfordia fruticosa* and tender shoots of plant *Camellia sinensis*.

In accordance with another embodiment of the present invention, there is provided a method of extraction of said plants employing organic solvents, selected from group comprising n-hexane, chloroform, dichloromethane, ethyl acetate, acetone, alcohol, methanol or water, either alone or in various combinations thereof.

In accordance with yet another embodiment of present invention, there is provided a method for extracting said plant extracts employing said solvents or a combination thereof, wherein obtained water extract of *Rhodomyrtus tomentosa* is more effective in the inhibition of the enzyme elastase, water extract of *Cipadessa baccifera* is more effective in the inhibition of the enzyme hyaluronidase, methanol extract of *Woodfordia fruticosa* is more effective in the inhibition of the enzyme collagenase and water extract of *Camellia sinensis* is effectively used as a potent antioxidant.

Further embodiment of the present invention provides a cosmeceutical herbal composition, wherein said con position is capable to increase the synthesis of collagen and decrease the depolymerisation of hyaluronic acid.

In yet another embodiment of the present invention, there is provided an in vitro method of testing elastase inhibitory activities of the said plant extracts.

In still another preferred embodiment of the present invention, there is provided the elastase inhibitory activity of the water extract of *Rhodomyrtus tomentosa*, wherein said extract is very effective at the concentration of 0.0325 mg/ml to 0.5 mg/ml for 100% of said inhibition.

In yet another preferred embodiment of the present invention, there is provided a successive fractionation of the water extract of *Rhodomyrtus tomentosa* to yield highly active methanol: water (3:1) soluble fraction EL-29/3 as potent elastase enzyme inhibitor.

In still another embodiment of the present invention, there is provided a process of purifying the fraction EL-29/3 by column chromatography to obtain fraction EL-29/503 eluted with chloroform:methanol (9:1) and EL-29/506 eluted with chloroform: methanol (1:1) as potent enzyme inhibitors.

In yet another embodiment of the present invention, there is provided the hyaluronidase inhibitory activity of the water extract of *Cipadessa baccifera*, wherein said extract is very effective at the concentration of 0.03906 mg/ml to 1.25 mg/ml for 50% of said inhibition.

In still another embodiment of the present invention, there is provided a process of successive solvent fractionation of water extract of *Cipadessa baccifera* to obtain the most active water-soluble fraction (HU-57/5) as hyaluronidase inhibitor.

In still another embodiment of the present invention, there is provided the collagenase inhibitory activity of the methanol extract of *Woodfordia fruticosa*, wherein said extract is very effective at the concentration of 0.0625 mg/ml to 0.5 mg/ml for 100% of said inhibition.

In yet another embodiment of the present invention, there is provided a process of purification by column chromatography to yield two active fractions CL-29/2 eluted with hexane: ethyl acetate (95:5) and CL-29/5 eluted with ethyl acetate (100%) as potent collagenase inhibitors.

In yet another embodiment of the present invention, there is provided the composition of herbal extract blend comprising the water extract of *Rhodomyrtus tomentosa* (30% on the basis of dry extract weight) as Elastase inhibitor, water extract of *Cipadessa baccifera* (30% on the basis of dry extract weight) as Hyaluronidase inhibitor, methanol extract of *Woodfordia fruticosa* (30% on the basis of dry extract weight) as Collagenase inhibitor and the water extract of *Camellia sinensis* (10% on the basis of dry extract weight) as Antioxidant.

In still another preferred embodiment of the present invention, there is provided the antioxidant potential of the active herbal composition, which comprises the water extract of *Rhodomyrtus tomentosa*, water extract of *Cipadessa baccifera* and methanol extract of *Woodfordia fruticosa*, alone or in combination thereof and water extract of *Camellia sinensis*.

In yet another preferred embodiment of the present invention, there is provided a herbal cosmeceutical skin care composition, wherein the preferable composition could be comprising equal parts of the water extracts of *Rhodomyrtus tomentosa* and *Cipadessa baccifera* and methanol extract of *Woodfordia fruticosa*. Additionally 10% of water extract of *Camellia sinensis* is added to increase overall antioxidant activity of the composition.

In yet another embodiment, there is provided a herbal cosmeceutical composition, wherein about 0.1% to 5% of the herbal composition is effective for various skin related problems, including facial wrinkles, in humans without any side effects.

In still another embodiment, there is provided a herbal cosmeceutical composition, wherein about 0.2% to 5% of the herbal extracts mixture can be used as active ingredients in any form of cosmeceutical formulations.

In accordance with still another embodiment of the present invention, there is provided a method for preparing said herbal cosmeceutical composition, wherein the method comprises extracting all or selected plant parts of said plants, alone or in combination thereof, by percolation, filtering the plant extract, concentrating the plant extract to dryness on rotatory evaporator or on steam bath at optimum temperature and producing a herbal composition comprising the said dry extract and cosmeceutically acceptable carriers.

In accordance with still another embodiment of the present invention, there is provided a method for preparing said herbal cosmeceutical composition, wherein the method comprises extracting all or selected plant parts of said plants, alone or in combination thereof, by hot soxhalation, filtering the plant extract, concentrating the plant extract to dryness on rotatory evaporator or on steam bath at optimum temperature and producing a herbal composition employing the said dry extract and cosmeceutically acceptable carrier.

In accordance with yet another embodiment of the present invention, there is provided a herbal cosmeceutical composition, wherein said composition is used in any topical form including creams, lotions, soaps, oils, sticks or sprays.

In still another embodiment, there is provided a method of preparation of a cream for topical application using the said herbal composition as an effective antiwrinkle agent and other cosmeceutically acceptable carriers.

In still another embodiment, there is provided a method of testing the efficacy of the said cream in prevention of wrinkle formation in rats when exposed to Ultra Violet radiation.

In yet another embodiment of the present invention, it is provided that the antiwrinkle formulation prevents transepidermal water loss and moisturizes the skin.

The disclosed antiwrinkle composition of the present invention decreases the depth and length of facial/periorbital fine wrinkles, also increases the skin firmness and elasticity and delays aging process and reverses their skin signs.

BRIEF DESCRIPTION OF THE DRAWINGS

Further objects of the present invention together with additional features contributing thereto and advantages accruing FIG. 1 Elastase inhibitory activity of EL-29 extract
FIG. 2 Hyaluronidase inhibitory activity of HU-57 extract
FIG. 3 Collagenase inhibitory activity of CL-29 extract
FIG. 4 HPLC chromatogram for standardization of EL-29 extract
FIG. 5 HPLC chromatogram for standardization of HU-57 extract
FIG. 6 HPLC chromatogram for standardization of CL-29 extract
FIG. 7 Antioxidant activity of AW-09 herbal composition
FIG. 8 Antioxidant activity of AW-09 herbal composition in ORAC assay
FIG. 9 Skin replica of normal animals showing least number of wrinkles
FIG. 10 Skin replica of UV exposed animals showing maximum number of wrinkles and maximum depth of wrinkles (Positive control).

DETAILED DESCRIPTION OF THE PRESENT INVENTION

Figure 1:
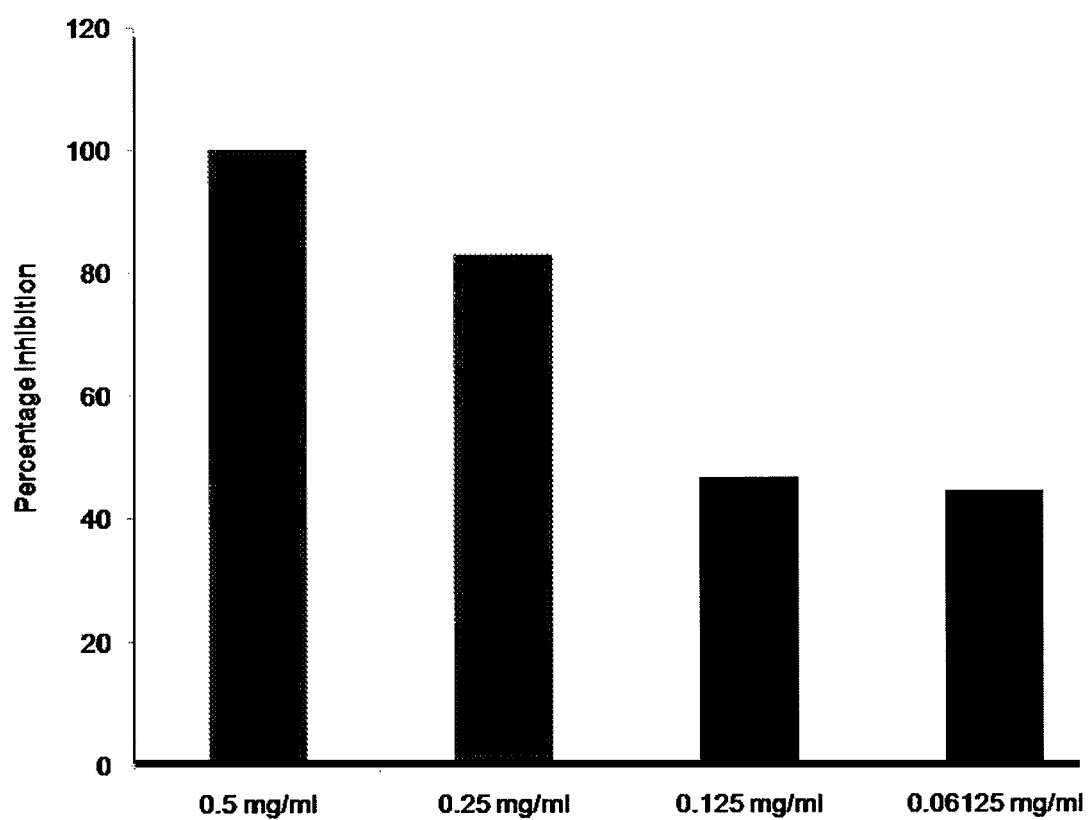

The present invention involves the selection of various herbs and obtaining the extract by subjecting the same to solvent extraction and screening of these extracts, in vitro, for the enzymes elastase, hyaluronidase and collagenase inhibitory activities. Preparation of a cosmeceutical composition using the effective herbal extracts in a particular ratio and other cosmeceutically acceptable carriers and evaluation of antiwrinkle activity in rats. The present cosmeceutical composition is effective to prevent wrinkle formation and other types of skin disorders due to aging and other environmental factors in humans.

*Rhodomyrtus tomentosa* Wight syn. *R. parviflora* Alston is a small genus of shrubs or trees, belongs to the family Myrtaceae and is distributed in the Indo-Malaysian region. Fruits are used for the treatment of diarrhea and dysentery and also eaten in anemia and for healing of wounds. A decoction of roots and leaves is reported for treating diarrhea and stomachache. The juice from pounded leaves is reported for anemia. In Indonesia, leaves are applied to wounds (Burkill, II, 1903-04; Brown, 1946, III, 155; *Nutritive Value of Indian Foods,* 74, 109, 137).

The plant contains phenolics. The phenolics and their salts are inhibitors of blood platelet aggregation and are calcium antagonists. Phenols of this plant are used in compositions to suppress bad mouth odours (Chem Abstr, 1992, 117, 245608; 1990, 112, 164767; Hajimohiddin et al, *Fitoterapia,* 1992, 30, 105).

*Cipadessa baccifera* (Roth) Miq. Syn. *C. fruticosa* Blume, a genus of shrubs or small trees, belongs to the family Meliaceae and is distributed in the Indo-Malaysian region. *C. baccifera* is a much-branched shrub up to 2.5 m in height with imparipinnate leaves, elliptic lanceolate leaflets, small white flowers in axillary corymbose panicles, and red globose berries, commonly found in parts of South India. The roots are used against tapeworms. The leaves make a poor fodder. The wood is used as fuel (*Bressers,* 27; Laurie, *Indian For. Leafl.* 1945, 82, 13)

*Woodfordia fruticosa* Kurz syn. *W. floribunda* Salish is a small genus of arborescent shrubs, belongs to the family Lythraceae and is distributed in tropical parts of Asia and Africa. The dried flowers are credited with stimulant and astringent properties, and are available in the market.

The leaves are reported to show antibiotic activity in vitro against *Micrococcus pyogenes* var. *aureus*. An extract of the flowers has shown activity against *Helminthosporium sativum*. The plant extract was also active against Ranikhet disease. (Joshi & Magar, *J. sci. industr. Res.,* 1952, 11B, 261; Bhatnagar et al., *Indian J med. Res.,* 1961, 49, 799; Dhar et al., *Indian J. exp. Biol.,* 1968, 6, 232).

*Camellia sinensis* Linn syn. *Camellia sinensis* Linn is an evergreen shrub or tree, belongs to the family Camelliaceae and is found from Assam and hilly regions to the east and south of it. It is also cultivated in the hilly districts of North and South India, and elsewhere for its leaves, which furnish the tea of commerce.

Polyphenols are the most important constituents in the tea leaf. More than three-quarters of the polyphenols in the leaf are flavanols, which are referred to as catechins. The flavanols identified include (+)- and (−)-catechin, (+)- and (−)-gallocatechin, (−)-catechin gallate, (−)-gallocatechin gallate, (−)-epiafzelechin, (−)-epicatechin and its gallate, and (−)-epigallocatechin and its gallate. Tea polyphenols protect ascorbic acid from oxidation in rat tissue homogenates because of their antioxidant properties.

Example-1

Preparation of Extract from *Rhodomyrtus tomentosa* by Percolation Method

The dried aerial parts of *Rhodomyrtus tomentosa* was pulverized to coarse powder and about 1 Kg each of powdered material placed in different flasks and extracted with n-hexane, dichloromethane, chloroform, ethyl acetate, acetone, ethanol, methanol and water at room temperature for 24 h to 48 h, then plant extracts were filtered and concentrated to dryness on rotatory evaporator or on steam bath at optimum temperature and under reduced pressure.

Example-2

Preparation of Extract from *Rhodomyrtus tomentosa* by Hot-Soxhalation Method

The dried aerial parts of *Rhodomyrtus tomentosa* was subjected to hot-soxhalation using solvents n-hexane, dichloromethane, chloroform, ethyl acetate, acetone, ethanol, methanol and water at optimum temperature and recycled until extraction is completed, then plant extracts were filtered and concentrated to dryness on rotatory evaporator or on steam bath at optimum temperature. All extracts were qualitatively similar to extracts prepared by percolation method.

Example-3

Preparation of Extract from *Cipadessa baccifera* by Percolation Method

The dried aerial parts of *Cipadessa baccifera* was pulverized to coarse powder and about 1 Kg each of powdered material placed in different flasks and extracted with n-hexane, dichloromethane, chloroform, ethyl acetate, acetone, ethanol, methanol and water at room temperature for 24 h to 48 h, then plant extracts were filtered and concentrated to dryness on rotatory evaporator or on steam bath at optimum temperature and under reduced pressure.

Example-4

Preparation of Extract from *Cipadessa baccifera* by Hot-Soxhalation Method

The dried aerial parts of *Cipadessa baccifera* was subjected to hot-soxhalation using solvents n-hexane, dichloromethane, chloroform, ethyl acetate, acetone, ethanol, methanol and water at optimum temperature and recycled until extraction is completed, then plant extracts were filtered and concentrated to dryness on rotatory evaporator or on steam bath at optimum temperature. All extracts were qualitatively similar to extracts prepared by percolation method.

Example-5

Preparation of Extract from *Woodfordia fruticosa* by Percolation Method

The dried fruits of *Woodfordia fruticosa* was pulverized to coarse powder and about 1 Kg each of powdered material placed in different flasks and extracted with n-hexane, dichloromethane, chloroform, ethyl acetate, acetone, ethanol, methanol and water at room temperature for 24 h to 48 h, then plant extracts were filtered and concentrated to dryness on rotatory evaporator or on steam bath at optimum temperature and under reduced pressure.

Example-6

Preparation of Extract from *Woodfordia fruticosa* by Hot-Soxhalation Method

The dried fruits of *Woodfordia fruticosa* was subjected to hot-soxhalation using solvents n-hexane, dichloromethane, chloroform, ethyl acetate, acetone, ethanol, methanol and water at optimum temperature and recycled until extraction is completed, then plant extracts were filtered and concentrated to dryness on rotatory evaporator or on steam bath at optimum temperature. All extracts were qualitatively similar to extracts prepared by percolation method.

Example-7

Preparation of Green Tea Extract (*Camellia sinensis*) by Percolation Method

The dried tender shoots of *Camellia sinensis* was pulverized to coarse powder and about 1 Kg each of powdered material placed in different flasks and extracted with n-hexane, dichloromethane, chloroform, ethyl acetate, acetone, ethanol, methanol and water at room temperature for 24 h to 48 h, then plant extracts were filtered and concentrated to dryness on rotatory evaporator or on steam bath at optimum temperature and under reduced pressure.

Example-8

Preparation of Green Tea Extract (*Camellia sinensis*) by Hot-Soxhalation Method The dried tender shoots of *Camellia sinensis* was subjected to hot-soxhalation using solvents n-hexane, dichloromethane, chloroform, ethyl acetate, acetone, ethanol, methanol and water at optimum temperature and recycled until extraction is completed, then plant extracts were filtered and concentrated to dryness on rotatory evaporator or on steam bath at optimum temperature. All extracts were qualitatively similar to extracts prepared by percolation method.

Example-9

Elastase Inhibition Assay with Insoluble Elastin

Elastase inhibitor activity was evaluated using elastase enzyme and elastin-congo red as substrate. The extent of dye release was measured as enzyme activity. Different concentrations of the extract were incubated with enzyme and substrate for 6 hrs. Inhibition of dye release from elastin cango red was considered to measure the elastase inhibitory activity. 250 μl of the reaction mixture contained 100 μl elastin-congo red, 50 μl of drug sample and 50 μl of tris buffer. The reaction was initiated by adding 10 μl of Elastase enzyme and after making up the volume to 250 μl with buffer the reaction mixture is incubated at 37° C. for 1-24 h. and the reaction is stopped by centrifugation at 30,000×g for 2 minutes and absorbance was read at 495 nm. Control samples are run without the drug.

All solvent extracts prepared from *Rhodomyrtus tomentosa, Cipadessa baccifera,* and *Woodfordia fruticosa* were subjected to elastase inhibitory activity. The water extract (EL-29) from *Rhodomyrtus tomentosa* was found to have highly potent elastase inhibitory activity. The elastase inhibitory activity of EL-29 was further tested at different concentrations and the results are shown in FIG. 1

Example-10

Hyaluronidase Inhibitory Activity

This assay was carried out in 96 well micro plate. Drug solutions were serially diluted with 0.02 M sodium phosphate buffer (pH 6.9) in the well and 30 μl of hyaluronic acid (1 mg/ml) was added as a substrate. Plate was read at 595 nm to record the initial reading. Incubated the mixture with freshly prepared hyaluronidase enzyme (30 μl, 200 IU/ml in 0.02 M sodium phosphate buffer with 1 mg BSA/ml) at 37° C. for 20 minutes. Then the reaction was stopped by adding 200 μl acid albumin solution (Acid Albumin Solution pH 3.72-3.78). Allowed it for 20 minutes at room temperature and read at 595 nm.

Figure 2:
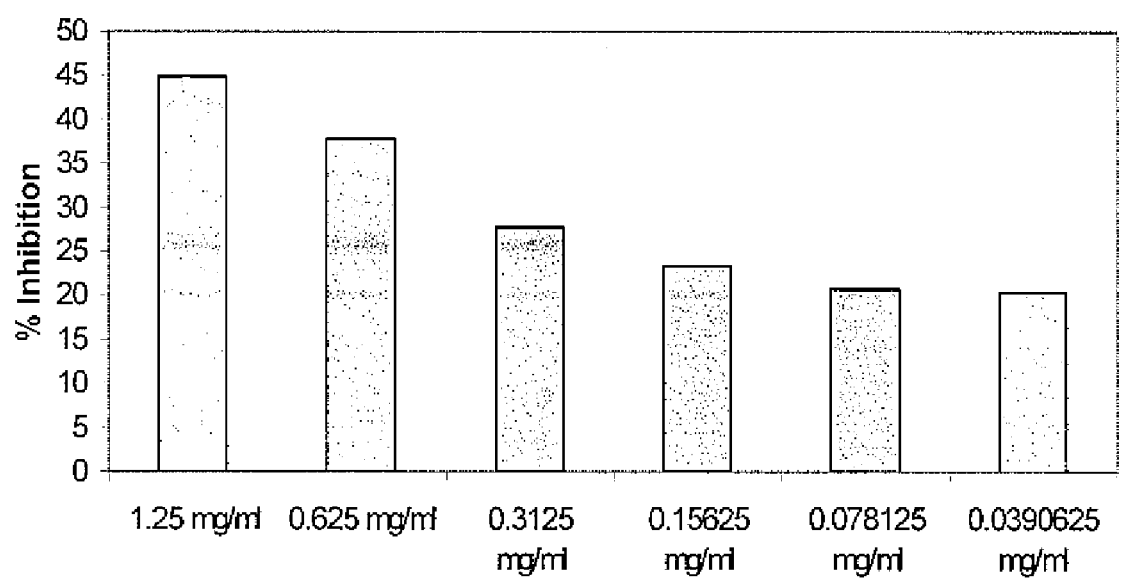

All solvent extracts prepared from *Rhodomyrtus tomentosa, Cipadessa baccifera,* and *Woodfordia fruticosa* were subjected to hyaluronidase inhibitory activity. The water extract (HU-57) from *Cipadessa baccifera* was found to have highly potent hyaluronidase inhibitory activity. The hyaluronidase inhibitory activity of HU-57 was further tested at different concentrations and the results are shown in FIG. 2.

Example-11

Collagenase Inhibitory Activity

Reaction was carried out in eppendorfs tubes, 500 µl drug solutions were serially diluted with 500 µl of Tris Buffer and 2.5 mg collagen was added to all the tubes, the tubes were incubated for equilibration at 37° C. The reaction was initiated by adding 10 µl Collagenase Enzyme. All the tubes were mixed well and incubated at 37° C.; contents were swirled for 10-15 seconds at 1.5 and 3.5 hours. After 5 hours, tubes were centrifuged at 5,000 rpm and the supernatant was taken for colour development. Control samples were run without drug and blank samples were run without drug and enzyme.

Colour Development:

20 µl of the supernatant was taken for colour development in a 96 well plate and to this 200 µl of Ninhydrin colour reagent was added and the plate was placed over boiling water bath for 20 min for the reaction to take place, after completion of the reaction the plate was cooled to room temperature. 50 µl of the reaction mixture was again taken in to another 96-well plate and to this 200 µl of 50% 1-propanol was added. The solution was mixed well and the absorbance was read at 570 nm. The percentage inhibition was calculated by using mean control absorbance value.

Figure 3:
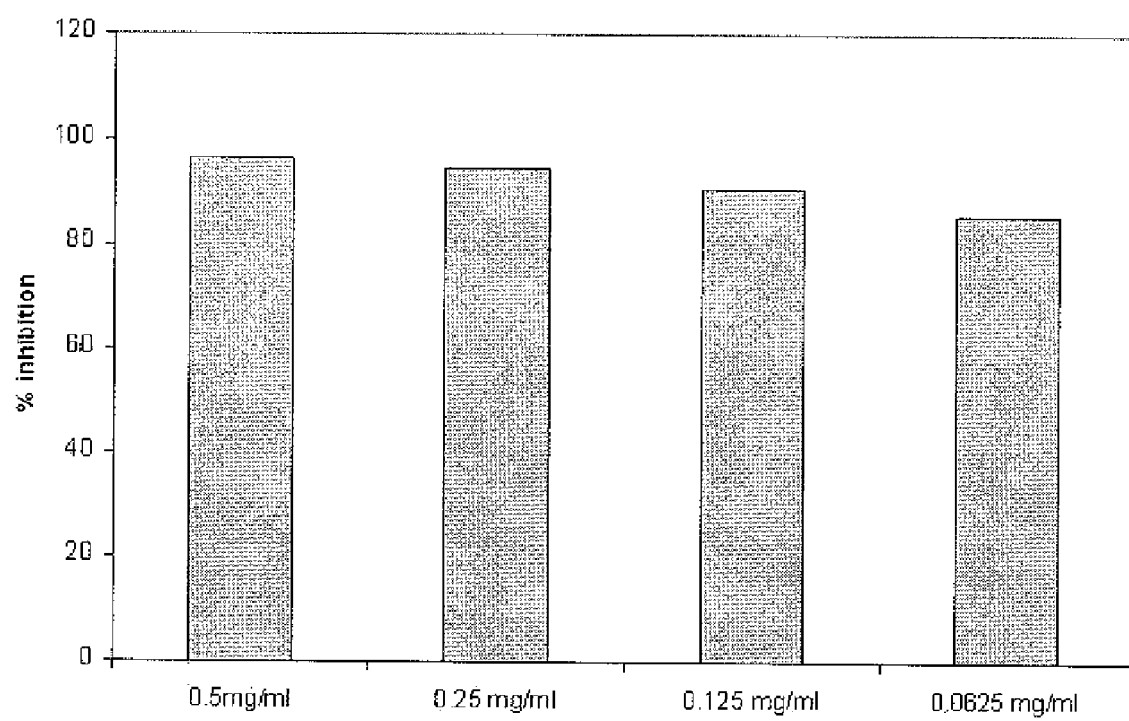

All solvent extracts prepared from *Rhodomyrtus tomentosa*, *Cipadessa baccifera*, and *Woodfordia fruticosa* were subjected to collagenase inhibitory activity. The methanol extract (CL-29) from Woodfordia fruticosa was found to have highly potent collagenase inhibitory activity. The collagenase inhibitory activity of CL-29 was further tested at different concentrations and the results are shown in FIG. 3.

Example-12

Fractionation of EL-29 Extract (Elastase Inhibitor)

About 100 g of water extract of *Rhodomyrtus tomentosa* (EL-29) was subjected to successive solvent fractionation into chloroform, methanol, methanol:water (75:25) and methanol: water (50:50) fractions. The extractive yields of the fractions are summarized in Table-1.

TABLE 1

| Sl. No. | Fraction Number | Nature of solvents | Yield (%) | Activity |
|---|---|---|---|---|
| 1 | EL-29/1 | Chloroform | 1 | Inactive |
| 2 | EL-29/2 | Methanol | 10 | Inactive |
| 3 | EL-29/3 | Methanol:Water(75:25) | 30 | Active |
| 4 | EL-29/4 | Methanol:Water (50:50) | 20 | Inactive |

Example-13

Column Chromatography of Fraction EL-29/3

The active fraction EL-29/3 (15 g) was subjected to column chromatography over silica gel (450 g, 60-120 mesh) using chloroform and methanol as eluting solvents with gradual increase in the polarity. About 75 fractions of 250 ml each were collected and combined based on thin layer chromatography (TLC) profile. The details of semi purified fractions and the activity are summarized in Table-2

TABLE 2

| Sl. No. | Code No | Nature of solvents | Activity profile |
|---|---|---|---|
| 1 | EL-29/501 | Chloroform:methanol (98:2) | Inactive |
| 2 | EL-29/502 | Chloroform:methanol (95:5) | Inactive |
| 3 | EL-29/503 | Chloroform:methanol (90:10) | Active |
| 4 | EL-29/504 | Chloroform:methanol (80:20) | Inactive |
| 5 | EL-29/505 | Chloroform:methanol (70:30) | Inactive |
| 6 | EL-29/506 | Chloroform:methanol (50:50) | Active |
| 7 | EL-29/507 | Methanol | Inactive |

Example-14

Standardization of EL-29 Extract/Fractions by TLC and HPLC

The thin layer chromatography of EL-29 extracts and semipurified fractions were performed over precoated silica gel plates (e-Merck) in mobile phase Ethylacetate: Formic Acid: Acetic Acid: Water (10:1:1:2.5). The plates were air dried and sprayed with 1% alcoholic ninhydrin solution and 1% alcoholic ferric chloride solution. The plates sprayed with ninhydrin reagent were dried in hot oven at 100° C. to give positive pink spots indicating the presence of amines, amino acids and peptides. The positive bluish spots with the ferric chloride reagent indicate the presence of phenolic compounds and glycosides.

Figure 4:
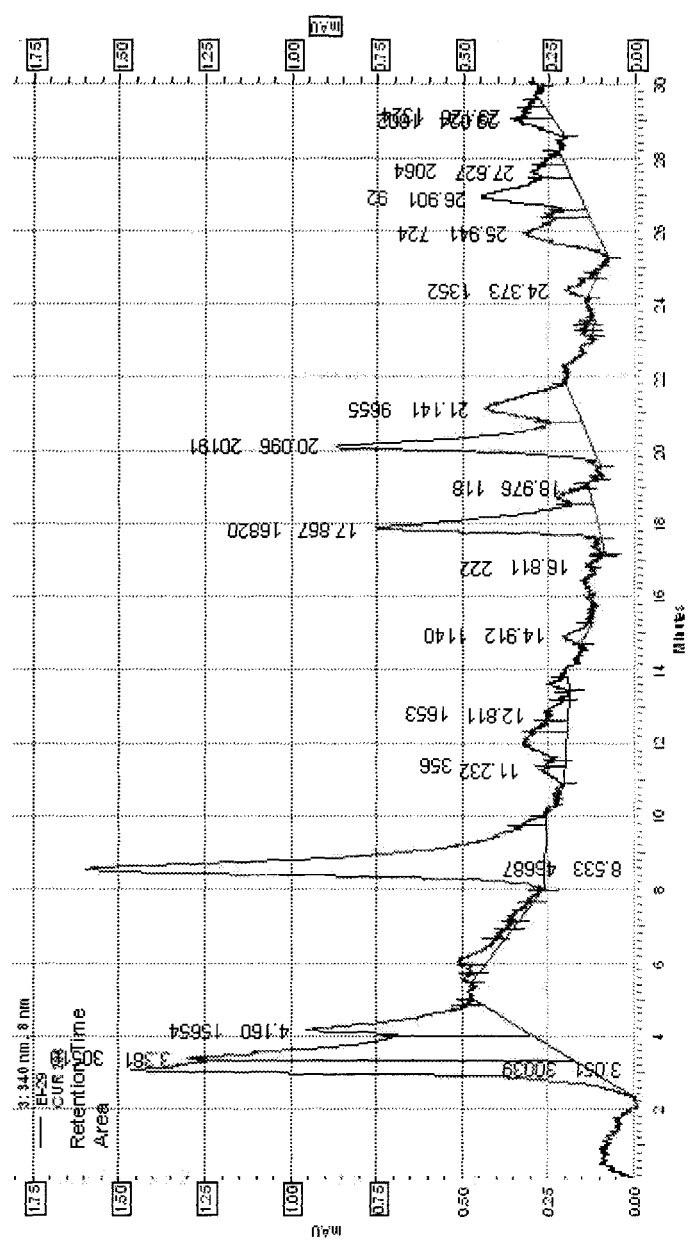

The active extract and fractions were standardized with HPLC (Shimadzu, LC-10A with PDA detector and C-18 reverse phase column) using mobile phase comprising solution A (1% Acetic acid in Water) and B (Methanol: Acetonitrile, 50:50) The analysis was done by using time program (Table-3) with 1 ml/min flow rate and detected at $\lambda_{max}$ 280 nm and 340 nm. The HPLC chromatogram of EL-29 is given as FIG. 4.

TABLE 3

| Time | A % | B % |
|---|---|---|
| 0.1 | 85 | 15 |
| 20 | 60 | 40 |
| 25 | 40 | 60 |
| 30 | 00 | 100 |
| 50 | 00 | 100 |

Example-15

Quantitative & Qualitative Estimation of Chemical Constituents of EL-29

The extract EL-29 was subjected to chemical identification methods (in house) to identify the nature and quantitative yields of different chemical nature of compounds and the results are given in the below table.

TABLE 4

| Sl. No. | Nature of constituents | Percentage (w/w) |
|---|---|---|
| 1 | Bitters | 4.12 |
| 2 | Alkaloids | 0.03 |
| 3 | Flavonoids | 2.34 |
| 4 | Saponins | 10.73 |
| 5 | Tannins | 36.33 |
| 6 | Glycosides | 17.76 |
| 7 | Procynadin value | 24.99 |

Example-16

Fractionation of HU-57 Extract (Hyaluronidase Inhibitor)

About 100 g of water extract of *Cipadessa baccifera* (HU-57) was subjected to successive solvent fractionation into chloroform, methanol, methanol: water (75:25) and methanol: water (50:50) and water fractions. The extractive yields of the fractions are summarized in Table-5.

TABLE 5

| Sl. No. | Fraction Number | Nature of solvents | Yield (%) | Activity |
|---|---|---|---|---|
| 1 | HU-57/1 | Chloroform | 1 | Inactive |
| 2 | HU-57/2 | Methanol | 5 | Inactive |
| 3 | HU-57/3 | Methanol:water (75:25) | 2 | Inactive |
| 4 | HU-57/4 | Methanol:water (50:50) | 7 | Inactive |
| 5 | HU-57/5 | Water | 85 | Active |

Example-17

Standardization of HU-57 Extract/Fractions by TLC and HPLC

The thin layer chromatography of HU-57 extract and fractions were performed over precoated silica gel plates (e-Merck) in mobile phase (1) n-Butanol: Formic Acid: Water (10:3:3) and (2) n-Butanol: Propanol: Acetic acid: water (3:1:1:1). The plates were air dried and sprayed with 1% alcoholic ninhydrin reagent and 1% alcoholic ferric chloride reagent and 1% alcoholic sulphuric acid reagent. The plates sprayed with ninhydrin reagent were dried in hot oven at 100° C. to give positive pink spots indicating the presence of amines, amino acids and peptides. The positive bluish spots observed with the ferric chloride reagent indicating the presence of phenolic compounds and glycosides. The positive black spots developed with the sulphuric acid reagent indicate the presence of terpenoids, glycosides and saponins, etc.

Figure 5:
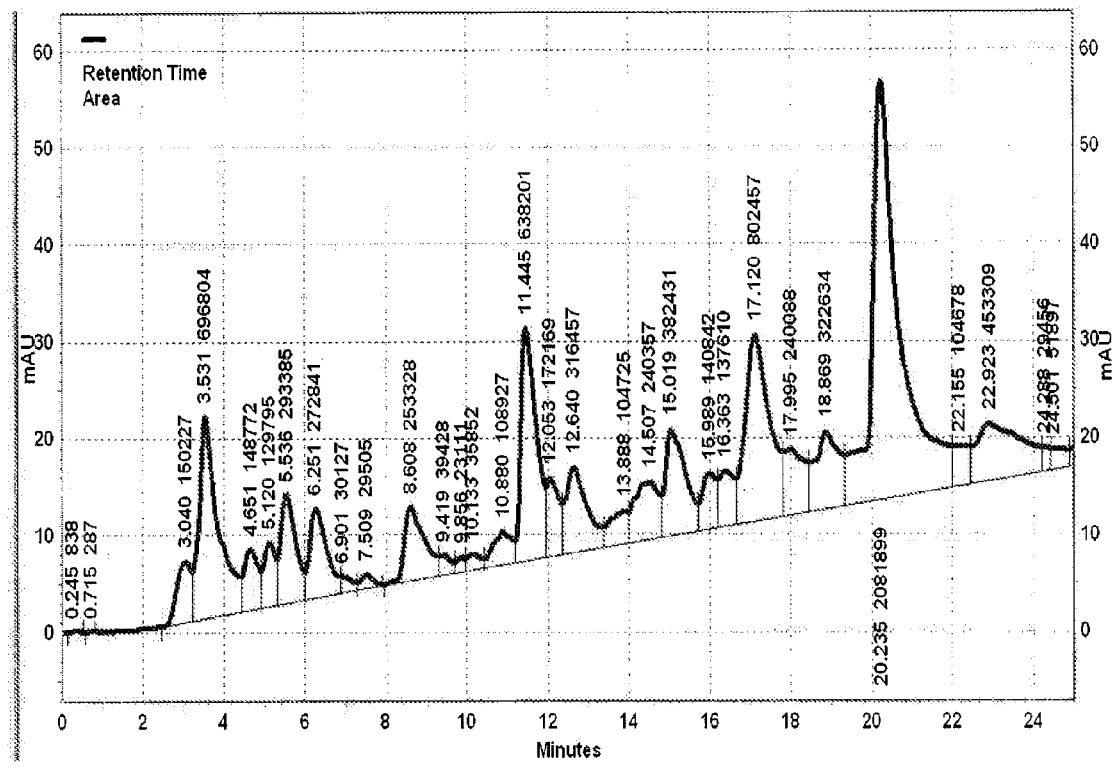

The active extract and fractions were standardized with HPLC (Shimadzu, LC-10A with PDA detector and C-18 reverse phase column) using mobile phase comprising solution A (0.1% Orthophosphoric acid in Water) and B (Acetonitrile). The analysis was done by using time program (Table-6) with 1 ml/min flow rate and detected at $\lambda_{max}$ 205 nm and 210 nm. The HPLC chromatogram of BU-57 is given as FIG. 5.

TABLE 6

| Time | A % | B % |
|---|---|---|
| 0.1 | 10 | 90 |
| 12 | 30 | 70 |
| 32 | 40 | 60 |

Example-18

Qualitative & Quantitative Estimation of Chemical Constituents of HU-57

The extract HU-57 was subjected to chemical identification methods (in house) to identify the nature and quantitative yields of different chemical nature of compounds and the results are given in the below Table-7.

TABLE 7

| Sl. No. | Nature of constituents | Percentage w/w |
|---|---|---|
| 1 | Bitters | 1.94 |
| 2 | Alkaloids | 0.015 |
| 3 | Flavonoids | 0.43 |
| 4 | Saponins | 9.14 |
| 5 | Tannins | 14.63 |
| 6 | Glycosides | 19.86 |
| 7 | Procynadin value | 21.19 |

Example-19

Preparation of Semi Purified Fractions from CL-29 by Column Chromatography

The active extract CL-29 (20 g) was subjected to column chromatography over silica gel (600 g, 60-120 mesh) using n-hexane, ethyl acetate and methanol as eluting solvents with gradual increase in the polarity. About 105 fractions of 250 ml each were collected and combined based on thin layer chromatography (TLC) profile. The details of semi purified fractions and the activity are summarized in Table-8

TABLE 8

| Sl No | Code No | Nature of solvents | Nature of fraction | Activity profile |
|---|---|---|---|---|
| 1 | CL-29/1 | Hexane: ethylacetate (95:5) | Yellowish oil | Inactive |
| 2 | CL-29/2 | Hexane: ethylacetate (95:5) | Yellowish powder | Active |
| 3 | CL-29/3 | Hexane: ethylacetate (90:10) | Green Viscousmass | Inactive |
| 4 | CL-29/4 | Hexane: ethylacetateto (50:50) | Green Viscousmass | Inactive |
| 5 | CL-29/5 | Ethylacetate | Brown Viscous mass | Most active |
| 6 | CL-29/6 | Ethylacetate: methanol(90:10) | Dirty white powder | Inactive |
| 7 | CL-29/7 | Ethylacetate: methanol(75:25) | Brown hygroscopic | Inactive |
| 8 | CL-29/8 | Ethylacetate: methanol(50:50) | Brown viscous matter | Inactive |
| 9 | CL-29/9 | Ethylacetate: methanol(25:75) | Brown matter | Inactive |
| 10 | CL-29/10 | Methanol | Red brown powder | Active |

Example-20

Standardization of CL-29 Extract/Fractions by TLC and HPLC

The thin layer chromatography of CL-29 extract and fractions were performed over precoated silica gel plates (e-Merck) in mobile phase (1) Benzene: methanol (7:3), (2) Chloroform: methanol (7.5:2.5), (3) Butanol: acetic acid: water (4:1:1). The plates were air dried and sprayed with 1% alcoholic ferric chloride reagent and 1% alcoholic sulphuric acid reagent. The positive bluish spots observed with the ferric chloride reagent indicating the presence of phenolic compounds and glycosides. The positive black spots developed with the sulphuric acid reagent indicating the presence of terpenoids, glycosides and saponins etc.

Figure 6:
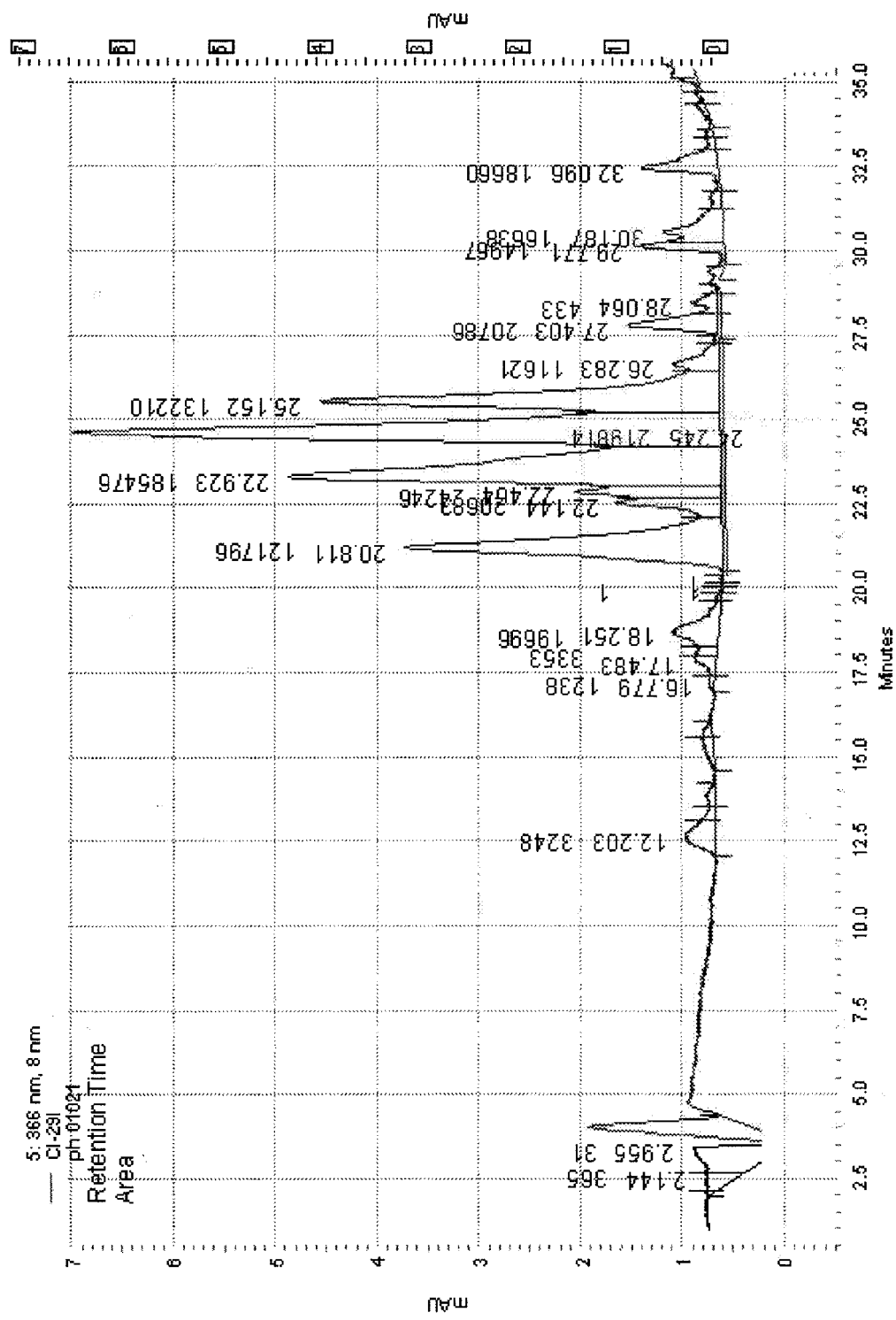

The active extract and fractions were standardized with HPLC (Shimadzu, LC-10A with PDA detector and C-18 reverse phase column) using mobile phase comprising solution A (0.1% Acetic acid in Water) and B (Methanol: Acetonitrile, 50:50). The analysis was done by using time program (Table-9) with 1 ml/min flow rate and detected at $\lambda_{max}$ 254 nm, 280 nm and 366 nm. The HPLC chromatogram of CL-29 is given as FIG. 6.

TABLE 9

| Time | A % | B % |
|---|---|---|
| 0.1 | 85 | 15 |
| 20 | 60 | 40 |
| 25 | 40 | 60 |
| 30 | 00 | 100 |
| 50 | 00 | 100 |

Example-21

Qualitative & Quantitative Estimation of Chemical Constituents of CL-29

The extract CL-29 was subjected to chemical identification methods (in house) to identify the nature and quantitative yields of different chemical nature of compounds and the results are given in the below Table-10.

TABLE 10

| Sl. No | Nature of constituents | Percentage w/w |
|---|---|---|
| 1 | Bitters | 9.00 |
| 2 | Alkaloids | 0.13 |
| 3 | Flavonoids | 1.97 |
| 4 | Saponins | 13.37 |
| 5 | Tannins | 15.90 |
| 6 | Glycosides | 16.98 |
| 7 | Procynadin value | 5.57 |

Example-22

Preparation of Bioactive Extract Composition for Antiwrinkle Formulation

Among all solvent extracts prepared from *Rhodomyrtus tomentosa, Cipadessa baccifera* and *Woodfordia fruticosa* for testing enzyme inhibitory activities, the water extract of *Rhodomyrtus tomentosa*, the water extract of *Cipadessa baccifera* and methanol extract of *Woodfordia fruticosa* were found to be potent inhibitors for enzymes elastase, hyaluronidase and collagenase respectively. The following composition coded as AW-09 (Table-11) was prepared as an effective concentration for preventing wrinkle formation due to aging process and all types of other skin disorders due to aging and environmental factors.

TABLE 11

| Sl. No. | Plant Name | Extract | Concentration (Percentage) | Indication |
|---|---|---|---|---|
| 1. | Rhodomyrtus tomentosa | Water | 30 | Elastase Inhibitor |
| 2. | Cipadessa baccifera | Water | 30 | Hyluronidase Inhibitor |
| 3. | Woodfordia fruticosa | Methanol | 30 | Collagenase Inhibitor |
| 4. | Camellia sinensis | Water | 10 | Antioxidant |

Example-23

Antioxidant Activity of AW-09 (Antiwrinkle) Composition

Figure 7:
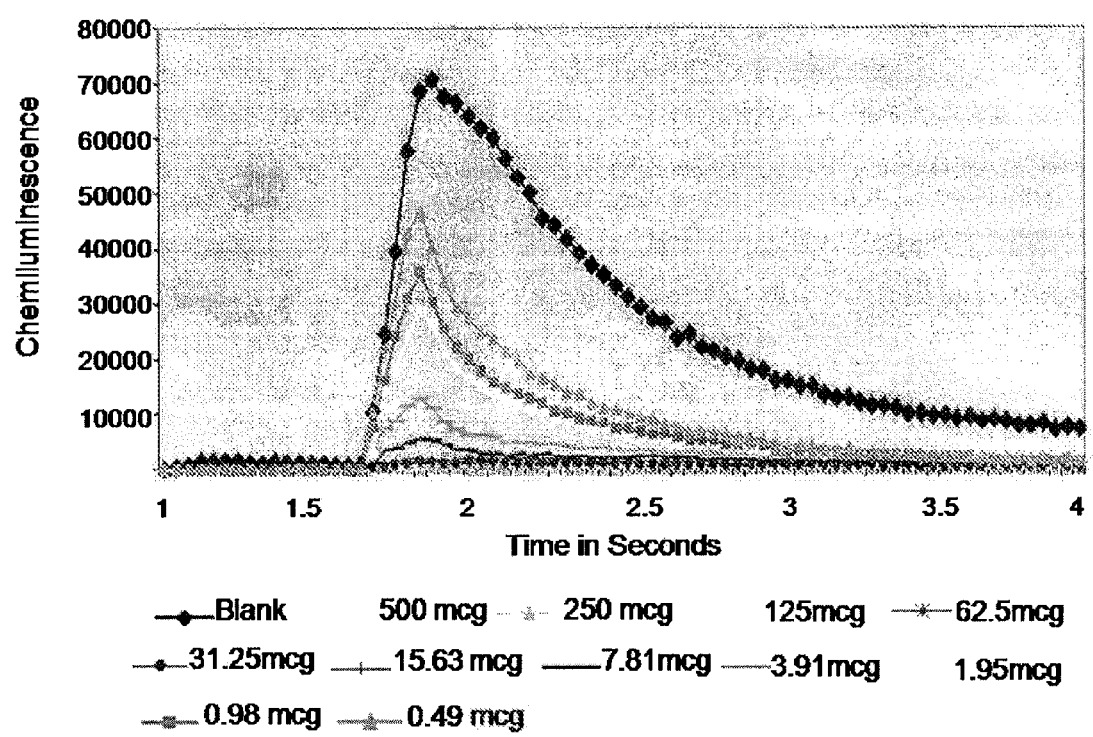

In a 96 well plate, each well was loaded with 100 μl of phosphate buffer. The test drug at different concentrations is added to each well except the first well, which served as positive control. 100 μl of 1.0 mM luminol in 0.1 N NaOH was added to all the wells. Initial chemiluminescence i.e. before adding $H_2O_2$ was recorded. 25 μl of 10 mM $H_2O_2$ is added to the wells to initiate the reaction and chemiluminescence was recorded for 4-5 seconds in flash mode. Results are given in FIG. 7.

Oxygen Radical Absorbance Capacity (ORAC) Assay

Figure 8:
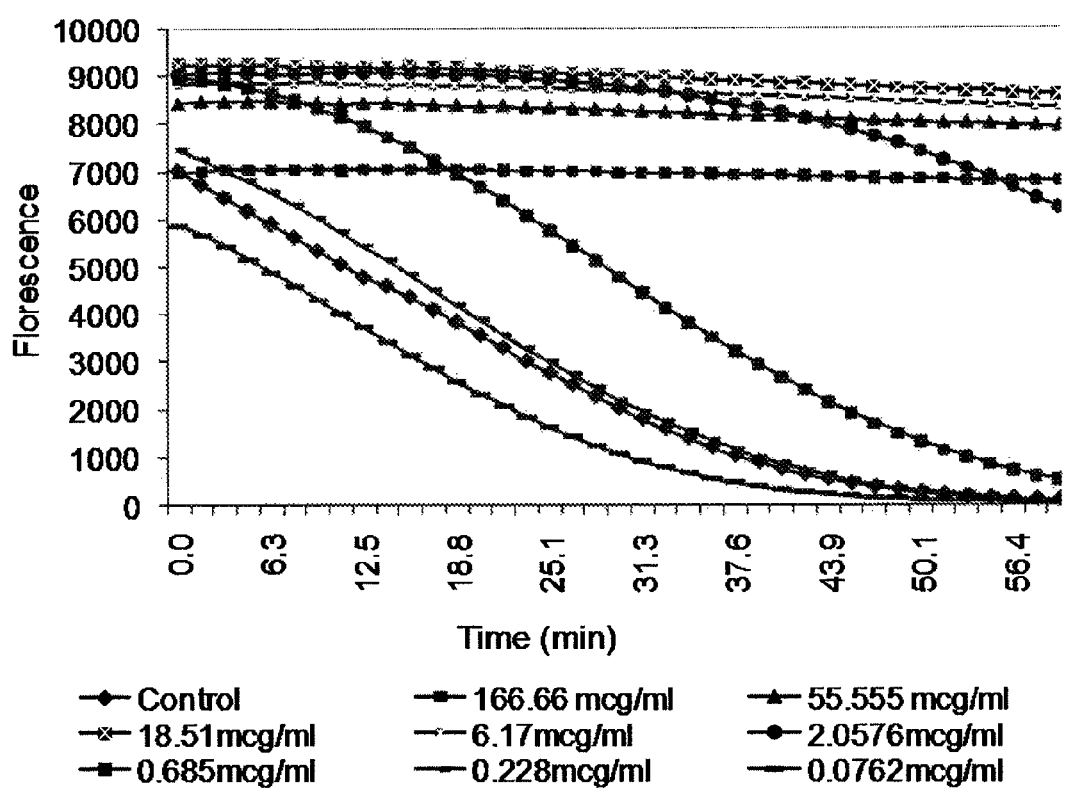
Figure 9:
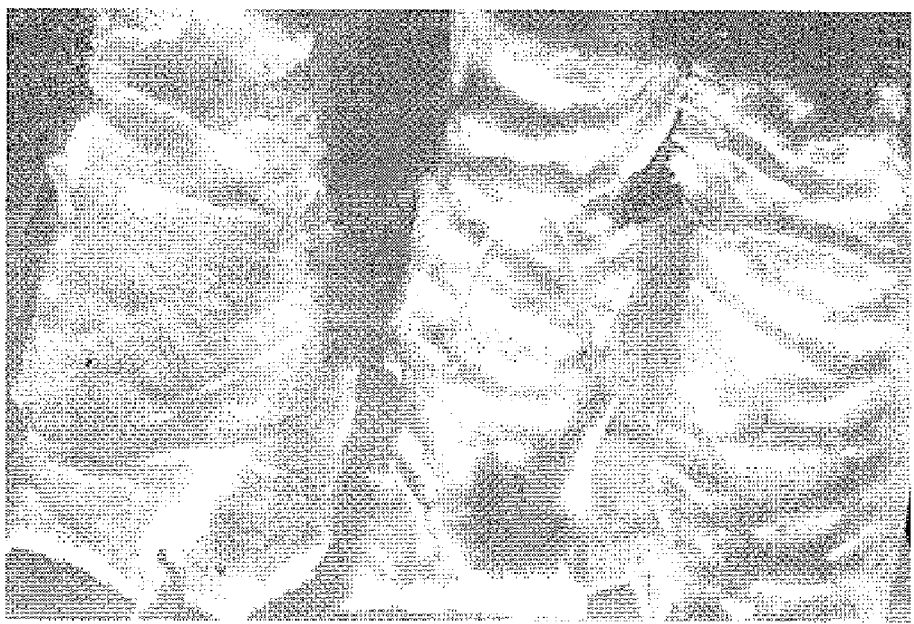
Figure 10:
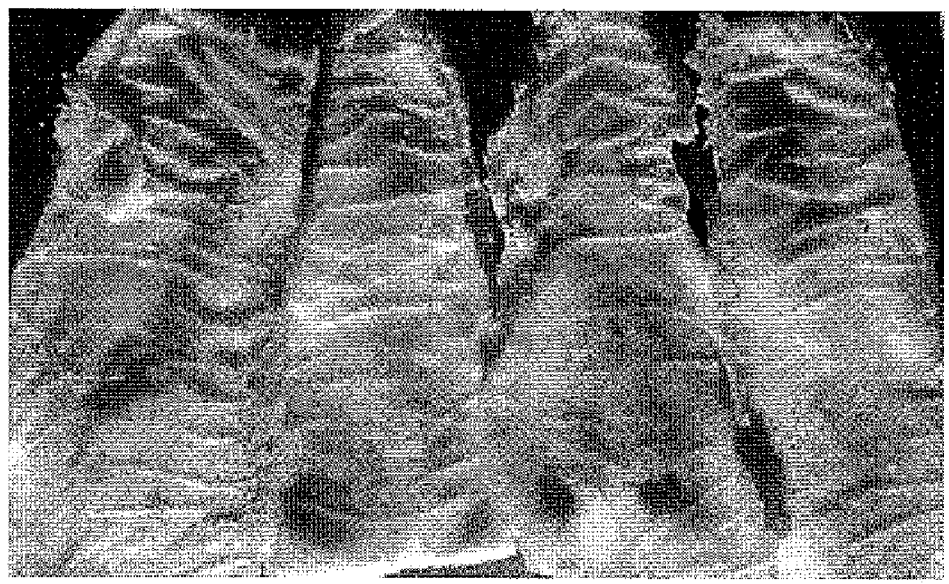
Figure 11:
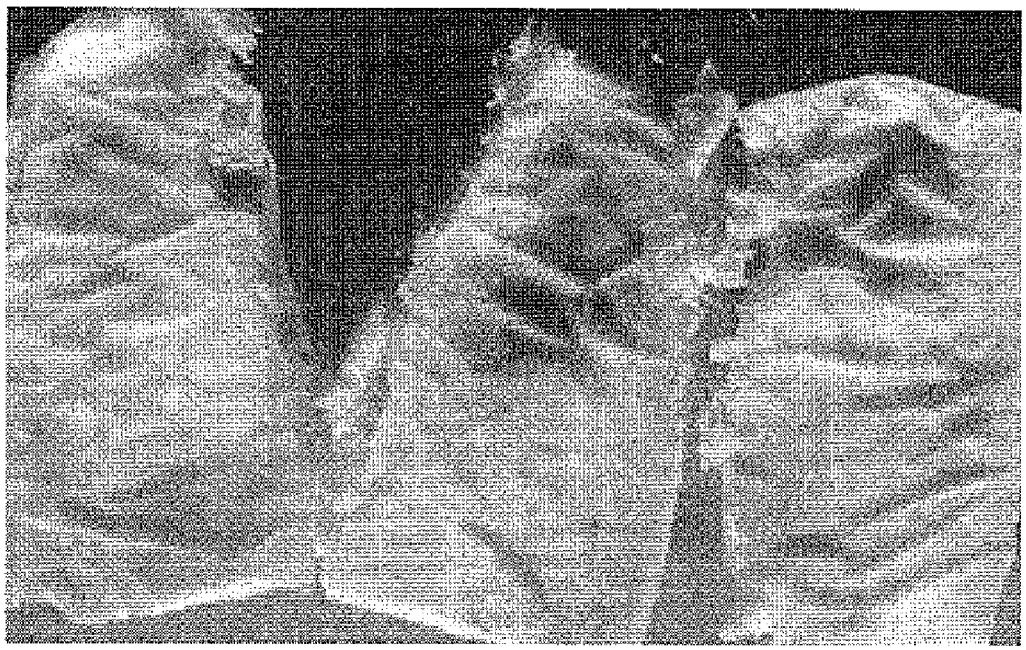
FIG. 11 Skin replica of UV exposed animals showing protection against UV induced wrinkles by treatment with AW-09 cream.
Figure 12:
FIG. 12 Skin replica of UV exposed animals showing moderate protection against UV induced wrinkles by treatment with competitive market antiwrinkle product.
Figure 13:
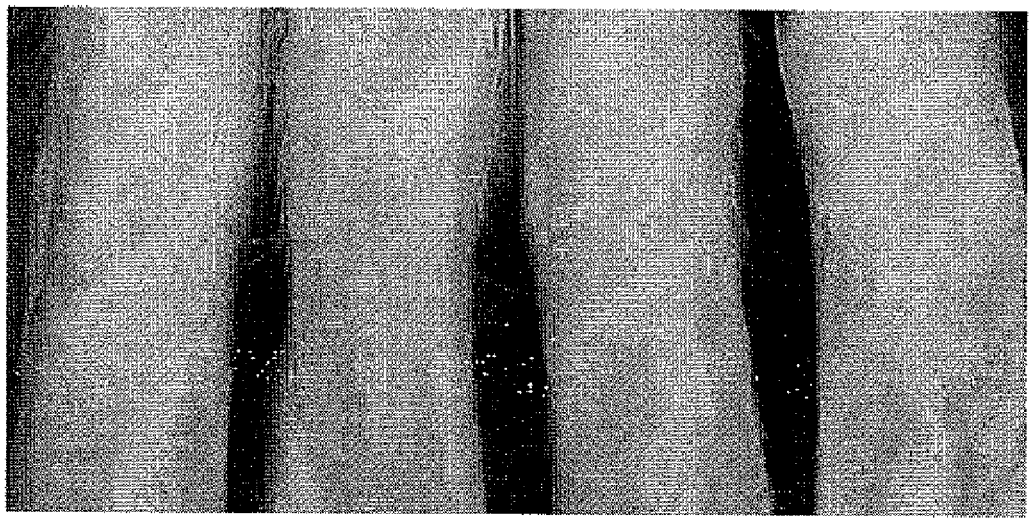
FIG. 13 Skin surface of normal animals showing least number of wrinkles
FIG. 14 Skin surface of UV exposed animals showing maximum number of and depth of wrinkles. (Positive control)
FIG. 15 Skin surface of UV exposed animals showing maximum protection to UV induced wrinkles by treatment with AW-09 cream
FIG. 16 Skin surface of UV exposed animals showing moderate protection to UV induced wrinkles by treating with competitive market product.
Figure 14:
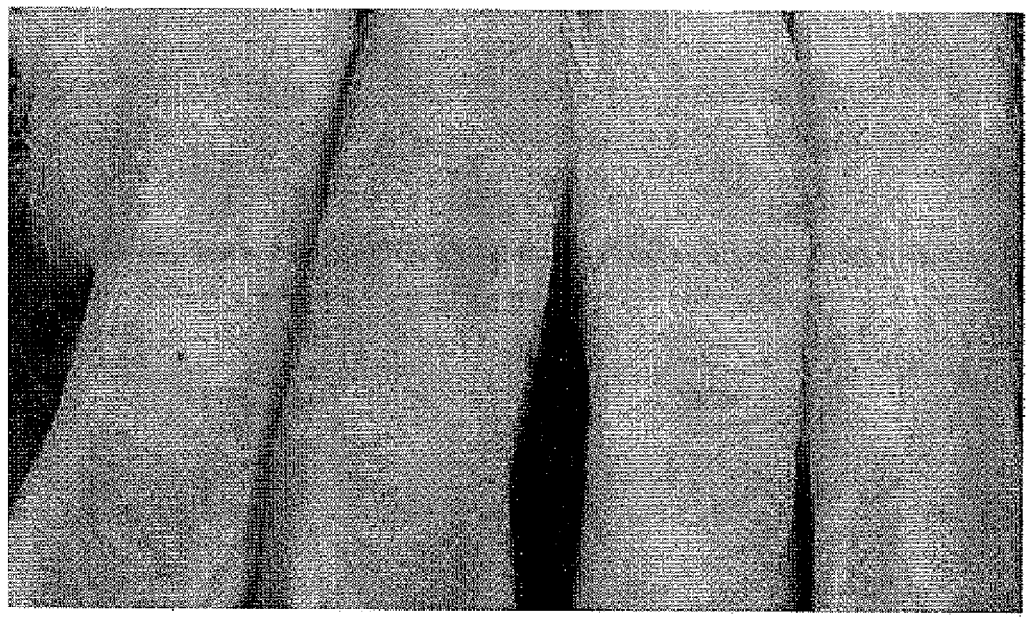
Figure 15:
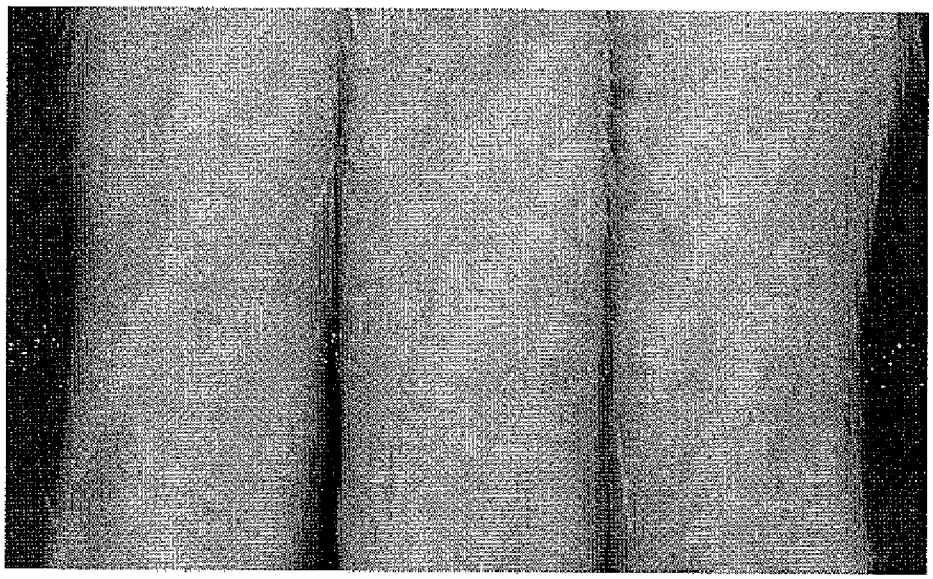
Figure 16:
Figure 17:
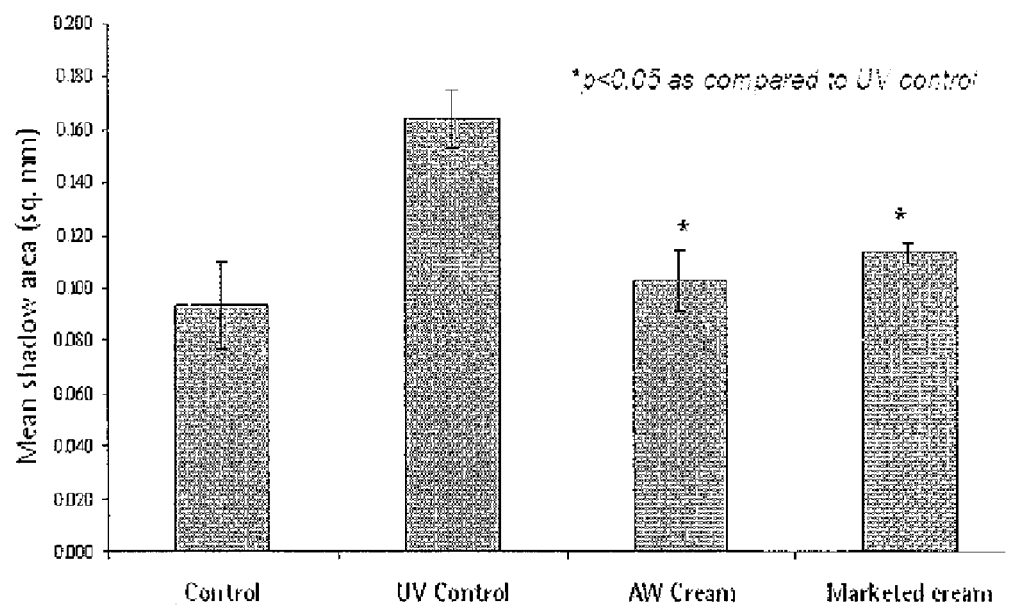
FIG. 17 Effect of AW-09 cream against UV induced wrinkles in rats (Showing mean shadow index).
Figure 18:
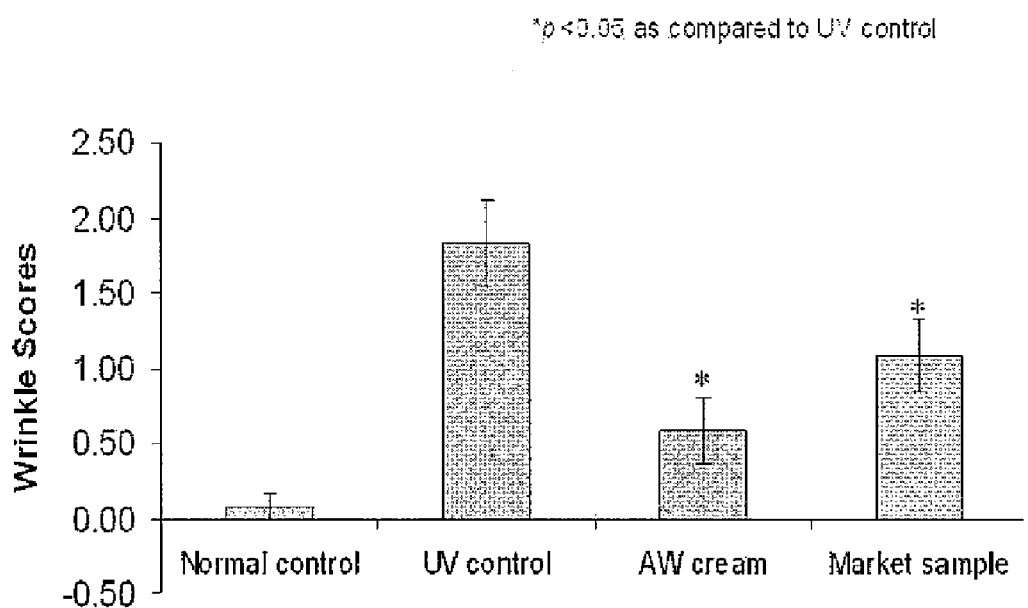
FIG. 18 Effect of AW-09 cream against UV induced wrinkles in Rats (No. of wrinkles).
Figure 19:
FIG. 19 Photograph showing Section of skin showing normal structure and architecture.
Figure 20:
FIG. 20 Photograph showing Section of skin from UV exposed group showing severe degree of elastosis.
Figure 21:
FIG. 21 Photograph showing Skin section from AW-09 cream treated group showing complete absence of elastosis.
Figure 22:
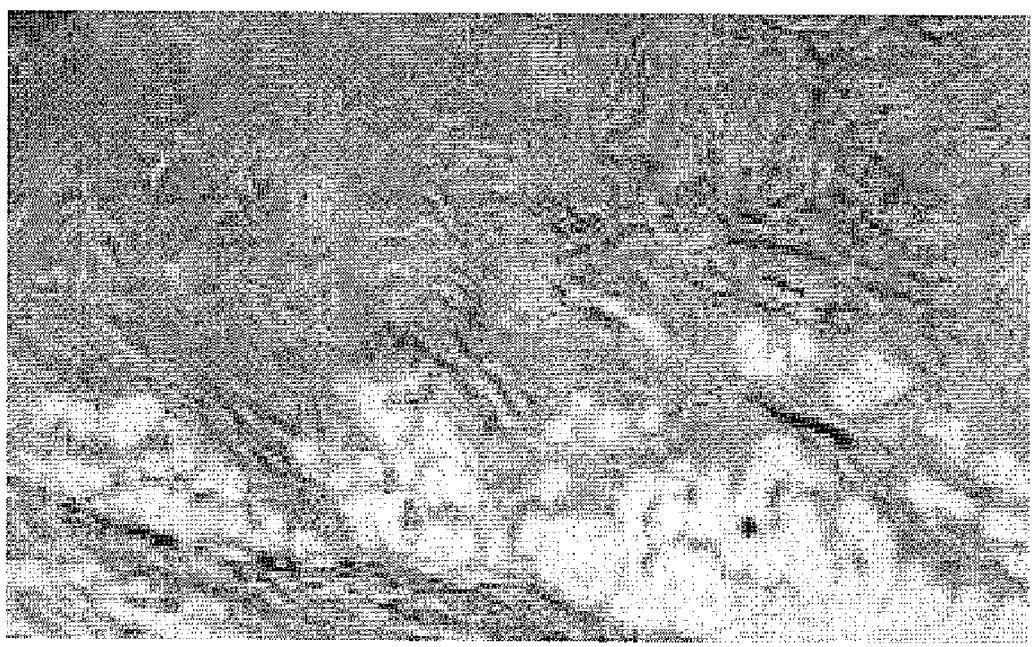
FIG. 22 Photograph showing Skin section from competitive market product treated group showing moderate degree of elastosis.

This assay quantitatively measures the total antioxidant capacity as well as qualitatively measures the amount of fast vs. slow acting antioxidants in the sample to be tested. The assay measures the effectiveness of various natural antioxidants, present in the sample, in preventing the loss in the fluorescence intensity of the fluorescent marker fluorescein, during peroxy radical induced {2,2'-azobis(2-amido-propane) dihydrochloride (AAPH)} free radical damage. Allowing the reaction to reach completion and then integrating the area under the kinetic curve relative to a blank reaction containing no added antioxidants to quantify assay results. Results are given in FIG. 8.

Example-24

Preparation of Antiwrinkle Cream (AW-09 Cream)

The antiwrinkle cream was prepared using AW-09 from 0.5% to 5% as effective therapeutic concentration along with other cosmeceutically acceptable carriers, Glycerol Mono Hydroxy Stearate, Glycerine, Light Liquid paraffin, Petroleum jelly, Cetyl alcohol, Polysorbate 60, Sorbitan stearate, Polyethoxylated alcohol, Isopropyl Myristate, Natural Preservative, Di sodium EDTA, Caprylic Capric Triglyceride, BHT, Phenoxyethanol and natural Perfume.

Example-25

Evaluation of Antiwrinkle Activity of AW-09 Cream in Rats Animals

Male Sprague Dawley (SD) rats (200-200 g), were used for the study. Animals were housed and acclimatized to a constant temperature of 22±2° C. and were exposed to 12 hours of day and night cycle and were fed with standard rat feed and water ad libitum.

Radiation Source

Rats were placed in cages and irradiated by a bulb of 5 Toshiba SE lamps (UVB) without any filtering, for a total of 6 weeks. The distance from the lamp to the animal's hind limbs was 42 cm (irradiance was approximately 0.72 $mW/cm^2$), and a dose of 130 $mJ/cm^2$ (rat 1 sub erythemal dose 5170 $mJ/cm^2$) was given three times weekly for 10 minutes.

Method

Rats were divided into 7 groups of 6 rats each. Group 1: served as negative control; animals of this group were not exposed to UVB light or treated topically with any material. Group 2: was treated with cream base and serve as positive control, Group-3 and 4 were treated with AW-09 cream and competitive Marketed antiwrinkle cream respectively. Sample was applied topically to the hind limbs 5 times a week for 12 weeks and animals were exposed to UV light 5 days a week for 10 min for 12 weeks.

Wrinkle Scoring and Image Analysis

The following measurements were performed under urethane anesthesia. Wrinkles in the rat hind limb skin were assessed according to the following method (grade 0: no coarse wrinkles, grade 1: a few shallow coarse wrinkles, grade 2: some coarse wrinkles, grade 3: several deep coarse wrinkles). A photograph of each rat hind limb was taken. Skin impression replicas were made of the hind limb skin using silicon impression material. The impression replicas were set on the sample stand so that the measurement surface is horizontal, and wrinkle shadows were produced by illumination with light of a fixed intensity at an angle of 30 degrees, using a fiber optic light source. The shadow images at the center of the hind limb skin were photographed with a digital camera. Binary images were obtained by extracting shaded areas of each image at a constant gray level. The shadow area is measured for all shadows in one image, using the image analyzer, and calculated the wrinkle area in sq mm (%). The results are given as FIG. 9-18.

Histology

For light microscopy, skin specimens obtained from rat hind limbs were fixed with formalin and embedded in paraffin. Specimen sections were cut and then stained with hematoxylin and eosin (H&E), and Luna. Histological pictures are given in FIG. 19-22.

Statistical Analysis

The values are expressed as Mean±SEM. The results were analyzed statistically using one-way ANOVA followed by Post Bonferroni's multiple comparison tests using Prism software package to find out the level of significance. The minimum level of significance was fixed at $p<0.05$.

Results

The present study demonstrated that the antiwrinkle cream AW-09 was significantly prevented the UV induced wrinkle formation in animals. The individual plant extracts EL-29, HU-57 and CL-29 are found to be potent inhibitors of the enzyme elastase, hyaluronidase and collagenase. The active composition AW-09 has also shown very potential antioxidant activity in in vitro models. The antiwrinkle activity of the cream AW-09 was evidenced by qualitative, quantitative and histological evaluation of skin sample. A competitive market sample, which was used as reference, showed mild to moderate protection. The antiwrinkle activity of AW-09 was shown in FIG. 17 (mean shadow index) and FIG. 18 (number of wrinkles).

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. An herbal cosmeceutical composition for decreasing occurrence of or treating; wrinkles, skin roughness and dryness of skin, wherein said composition comprises, in an effective concentration;
   a combination of a water extract of an aerial part of *Rhodomyrtus tomentosa*,
   a water extract of an aerial part of *Cipadessa baccifera*,
   a methanol extract of a fruit of *Woodfordia fruticosa*,
   a water extract of a tender shoot of *Camellia sinensis* as an antioxidant; and
   cosmeceutically acceptable carriers.

2. The herbal cosmeceutical composition according to claim 1, wherein said composition comprises equal parts of water extract of an aerial part of *Rhodomyrtus tomentosa*, water extract of an aerial part of *Cipadessa baccifera* and methanol extract of a fruit of *Woodfordia fruticosa* and 10% of water extract of a tender shoot of *Camellia sinensis* to increase overall antioxidant activity of the composition.

3. The herbal cosmeceutical composition according to claim 1, wherein said composition is capable of inhibiting the enzymes elastase, hyaluronidase, and collagenase, and decreasing the formation of ROS (Reactive Oxygen Species).

4. The herbal cosmeceutical composition according to claim 1, wherein said composition is capable of increasing the synthesis of collagen and also decreasing the depolymerisation of hyaluronic acid.

5. The herbal cosmeceutical composition according to claim 1, wherein said composition is in a topical form selected from a cream, a lotion, a soap, an oil, a stick or a spray.

6. The herbal cosmeceutical composition according to claim 1, wherein the water extract of an aerial part of *Rhodomyrtus tomentosa* is capable of inhibiting the enzyme elastase.

7. The herbal cosmeceutical composition according to claim 1, wherein the water extract of an aerial part of *Cipadessa baccifera* is capable of inhibiting the enzyme hyaluronidase.

8. The herbal cosmeceutical composition according to claim 1, wherein the methanol extract of a fruit of *Woodfordia fruticosa* is capable of inhibiting the enzyme collagenase.

9. The herbal cosmeceutical composition according to claim 1, wherein said extracts of *Rhodomyrtus tomentosa*, *Cipadessa baccifera*, *Woodfordia fruticosa* and *Camellia sinensis* are present at a concentration of 0.2% to 5% by weight of the composition.

10. A method of producing the herbal cosmeceutical composition of claim 1, the method comprising:
    extracting an aerial part of *Rhodomyrtus tomentosa* with water,
    extracting an aerial part of *Cipadessa baccifera* with water,
    extracting a fruit of *Woodfordia fruticosa* with methanol,
    extracting a tender shoot of *Camellia sinensis* with water,
    filtering all of said plant extracts,
    concentrating all of said filtered extracts to dryness using a rotatory evaporator or using a steam bath,
    drying all of said concentrated extracts,
    combining all of said dried extracts and
    adding cosmeceutically acceptable carriers to the combined extracts;
    wherein all of said extracting steps are carried out by percolation.

11. A method of producing the herbal cosmeceutical composition of claim 1, the method comprising:
    extracting an aerial part of *Rhodomyrtus tomentosa* with water,
    extracting an aerial part of *Cipadessa baccifera* with water,
    extracting a fruit of *Woodfordia fruticosa* with methanol,
    extracting a tender shoot of *Camellia sinensis* with water,
    filtering all of said plant extracts,
    concentrating all of said filtered extracts to dryness using a rotatory evaporator or using a steam bath,
    drying all of said concentrated extracts, combining all of said dried extracts and adding cosmeceutically acceptable carriers to the combined extracts;
    wherein all of said extracting steps are carried out by hot soxhalation.

* * * * *

UNITED STATES PATENT AND TRADEMARK OFFICE
CERTIFICATE OF CORRECTION

| | | |
|---|---|---|
| PATENT NO. | : 8,142,818 B2 | |
| APPLICATION NO. | : 12/440917 | |
| DATED | : March 27, 2012 | |
| INVENTOR(S) | : Shankar Kumar Mitra et al. | |

It is certified that error appears in the above-identified patent and that said Letters Patent is hereby corrected as shown below:

On the Title page, (Item 56), Line 19, Under Other Publications, change "Napal;" to --Nepal;--.

On the Title page, (Item 56), Line 21, Under Other Publications, change "Culd" to --Could--.

At Page 2, (Item 56), Line 3, Under Other Publications, change "Napal;" to --Nepal;--.

At Column 1, Line 11, Change "hut" to --but--.

At Column 3, Line 21, Change "con position" to --composition--.

At Column 3, Line 40, Change "chloroform:methanol" to --chloroform: methanol--.

At Column 4, Line 9 (Approx.), Change "thereof" to --thereof,--.

At Column 4, Line 40, Change "soxhalation," to --soxhlation,--.

At Column 6, Line 25, Change "13)" to --13).--.

At Column 6, Line 37 (Approx.), Change "J med." to --J. med.--.

At Column 7, Lines 3-4, Change "Hot-soxhalation" to --Hot-soxhlation--.

At Column 7, Line 6, Change "hot-soxhalation" to --hot-soxhlation--.

At Column 7, Lines 30-31 (Approx.), Change "Hot-soxhalation" to --Hot-soxhlation--.

At Column 7, Line 33 (Approx.), Change "hot-soxhalation" to --hot-soxhlation--.

At Column 7, Line 58-59 (Approx.), Change "Hot-soxhalation" to --Hot-soxhlation--.

At Column 7, Line 61, Change "hot-soxhalation" to --hot-soxhlation--.

At Column 8, Lines 16-17, Change "Hot-soxhalation" to --Hot-soxhlation--.

At Column 8, Line 19, Change "hot-soxhalation" to --hot-soxhlation--.

At Column 8, Line 34, Change "cango" to --congo--.

At Column 8, Line 40, Change "1-24h." to --18-24h.--.

At Column 8, Line 50, Change "FIG. 1" to --FIG. 1.--.

At Column 9, Line 44 (Approx.), Change "methanol:water" to --methanol: water--.

At Column 9, Line 67, Change "Table-2" to --Table-2.--.

Signed and Sealed this
Fourteenth Day of August, 2012

David J. Kappos
*Director of the United States Patent and Trademark Office*

CERTIFICATE OF CORRECTION (continued)
U.S. Pat. No. 8,142,818 B2

At Column 10, Line 65, Change "Procynadin" to --Procyanidin--.

At Column 11, Line 48, Change "BU-57" to --HU-57--.

At Column 12, Line 9, Change "Procynadin" to --Procyanidin--.

At Column 12, Line 22, Change "Table-8" to --Table-8.--.

At Column 12, Line 33 (Approx.), Change "ethylacetateto" to --ethylacetate--.

At Column 13, Line 28 (Approx.), Change "Procynadin" to --Procyanidin--.

At Column 13, Line 53 (Approx.), Change "Hyluronidase" to --Hyaluronidase--.

At Column 16, Line 59, In Claim 11, Change "soxhalation." to --soxhlation.--.